United States Patent [19]

Herscovici

[11] Patent Number: 4,543,956
[45] Date of Patent: Oct. 1, 1985

[54] BIPHASIC CARDIAC PACER

[75] Inventor: Harry Herscovici, Miami Beach, Fla.

[73] Assignee: Cordis Corporation, Miami, Fla.

[21] Appl. No.: 613,888

[22] Filed: May 24, 1984

[51] Int. Cl.⁴ .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,924,641 | 12/1975 | Weiss | 128/419 PG |
| 4,114,627 | 9/1978 | Lewyn et al. | 128/419 PG |
| 4,300,566 | 11/1981 | Stindt et al. | 128/419 PG |
| 4,343,312 | 8/1982 | Cals et al. | 128/419 PG |

Primary Examiner—William E. Kamm
Attorney, Agent, or Firm—George H. Gerstman

[57] ABSTRACT

A biphasic cardiac pacer is provided having a novel system for detecting the evoked response from the heart after a stimulating pulse is applied. A relatively short, high absolute amplitude stimulating pulse is applied to the heart. Thereafter, a compensating pulse having an absolute amplitude that is smaller than the absolute amplitude of the stimulating pulse, and having a duration that is longer than the duration of the stimulating pulse, is provided. The stimulating pulse and compensating pulse together comprise a biphasic waveform that provides rapid electrode charge neutralization and enhances subsequent capture detection. The biphasic waveform is automatically and dynamically balanced so that the electrical charge of the stimulating pulse portion is equal to the electrical charge of the compensating pulse portion. After the compensating pulse is provided, the evoked response is detected using the same electrodes that are used for providing the stimulating and compensating pulses.

13 Claims, 6 Drawing Figures

BIPHASIC CARDIAC PACER

BACKGROUND OF THE INVENTION

The present invention concerns a cardiac pacer having a novel system for detecting the evoked response from a stimulation pulse applied to a chamber of the heart.

Closed loop cardiac pacing can be employed for the adjustment of stimulus intensity and rate by assessing the heart's electrical response to stimulation. This can be achieved either by employing additional electrodes for detecting the evoked response from the heart, or by electrically neutralizing the stimulating electrodes immediately after a stimulus to enable them to sense the evoked response. This neutralization is necessary because the delivery of the stimulus leaves the electrodes in a polarized state. In the presence of this depolarization it is difficult or even impossible to detect the evoked response without the electrode neutralization process.

The neutralization process involves charge compensation; it is a rapid restoration of the electrodes to their resting baseline potential. If the stimulus is capacitively coupled to its load, discharging the coupling capacitor in the reverse direction should restore the electrodes to their baselines. However, this process is too slow to allow detection of the evoked response which occurs well within the first 50 ms.

When some resistive elements are shunted by the closure of a switch following a stimulus, then the neutralization is accelerated by the shortened time-constant. This method is often referred to as "charge dump." This is neither sufficiently rapid, nor sufficiently complete for reliable detection of the evoked response.

It is, therefore, an object of the present invention to provide a system for detecting the evoked response in which the neutralization process is rapid, using a biphasic waveform technique, i.e., using a compensating current pulse that is transmitted in the opposite direction from the stimulating current pulse.

However, we have discovered that when a compensating current pulse fullows a stimulating pulse, the cathode current threshold rises. This implies increased current drain from the battery even beyond the charge necessary for compensation. It is, therefore, a further object of the present invention to reduce battery drain notwithstanding the use of a biphasic waveform technique.

Other objects and advantages of the present invention will become apparent as the description proceeds.

SUMMARY OF THE INVENTION

In accordance with the present invention, a method of detecting evoked response from the heart is disclosed, comprising the steps of providing a stimulating pulse, thereafter providing a compensating pulse having an absolute amplitude that is smaller than the absolute amplitude of the stimulating pulse, automatically and dynamically balancing the electrical charges of the stimulating pulse and the compensating pulse so that the respective electrical charges are substantially equal, and thereafter detecting the evoked response using the same electrodes that are used for providing the stimulating and compensating pulses.

In the illustrative embodiment, the electrical charge (i.e., the product of the current times duration) of the stimulating pulse is equal to the electrical charge of the compensating pulse. The stimulating pulse is a negative pulse, and has an absolute amplitude that is substantially greater than the amplitude of the compensating pulse, and has a duration that is substantially less than the duration of the compensating pulse. Since charge stimulation threshold decreases with the decrease of pulse duration, by reducing the stimulating pulse duration to a short value there is a reduction in battery current drain. In the illustrative embodiment, the compensating pulse is shaped to be relatively low in absolute amplitude and wide, for example, one-tenth in absolute amplitude and ten times the duration of the stimulating pulse.

In the illustrative embodiment, the charge of the compensation pulses is equalized to the charge of the stimulation pulse by integrating successively the stimulation pulse and the compensation pulse. Capture is detected by blanking the output of a capture detector for a predetermined time after the stimulating pulse is issued, and thereafter providing a time window for seeking the evoked response.

It has been found that the relatively short stimulating pulse duration requires a high stimulus current intensity. In accordance with the present invention, the stimulation pulse is provided by multiplying the pacer's battery voltage using a voltage multiplier.

For sufficient neutralization, we have found that precise charge compensation is required. In accordance with the present invention, the stimulation pulse and the compensation pulse are integrated by an integrator circuit whose input is from a 10 ohm resistor in series with the load. The compensation stops when the integrator returns to zero. The stimulating and compensating pulses are automatically provided with equal charges for any ratio between the amplitudes of the two pulses.

A more detailed explanation of the invention is provided in the following description and claims, and is illustrated in the accompanying drawings.

DETAILED DESCRIPTION OF THE ILLUSTRATIVE EMBODIMENT

Figure 1:
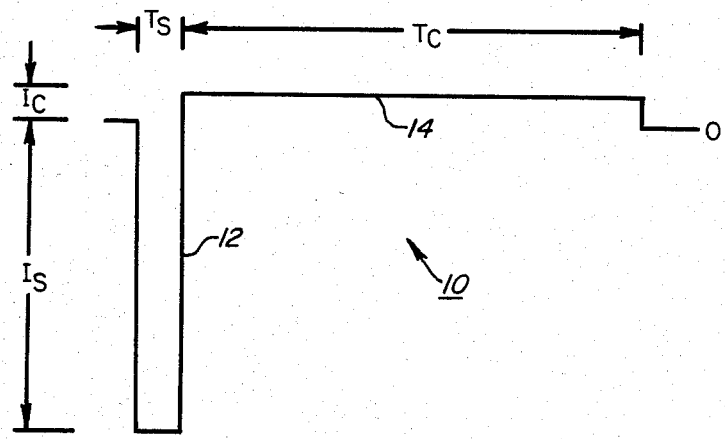
FIG. 1 is a diagram of a biphasic waveform generated by the cardiac pacer of the present invention.

Referring to FIG. 1, a biphasic waveform 10 is shown therein comprising a negative stimulating pulse 12 and a positive compensating pulse 14. The stimulating pulse has an absolute amplitude $I_s$ and a duration $T_s$. Compensating pulse 14, which is contiguous therewith, is in the opposite direction and has an absolute amplitude $I_c$ and a duration $T_c$. In accordance with the illustrative embodiment of the invention, biphasic waveform 10 is actively elaborated and automatically balanced for an accurate electrical charge compensation. The electrical charge of stimulating pulse 12 equals $I_sT_s$ and the electrical charge of compensating pulse 14 equals $I_cT_c$. In order to achieve a fast recovery after a pacer stimulus, the electrical charge of the stimulating pulse 12 should be equal to the electrical charge of the compensating pulse 14. In addition, in order to pace with biphasic waveforms without the use of too much extra energy from the battery, it is necessary that $I_c$ is substantially less than $I_s$. We have found that an appropriate relationship is for $I_c$ to equal $0.1I_s$ and for $T_c$ to equal $10T_s$.

We have also found that it is important for the stimulation pulse to have a relatively high amplitude $I_s$ (for example, 30 milliamps) and a very short duration $T_s$ (for example, 10 microseconds). This is because with biphasic waveforms the cathodal current threshold rises. Since charge stimulation threshold decreases with the decrease of pulse duration, a short duration pulse will compensate for the rise in threshold. Additionally, to produce a biphasic waveform, it is necessary to have extra energy from the battery and again the decrease in threshold with the decrease of pulse duration will help keeping the battery drain as low as possible.

It has also been found that as the stimulation pulse duration $T_s$ becomes shorter, the recovery becomes faster. We have found it to be a disadvantage to pace with a pulse duration $T_s$ that is wider than 0.5 milliseconds. For a pulse duration $T_s$ of 1.8 milliseconds, for example, the recovery time is almost six times longer than the recovery time with a pulse duration of 0.5 milliseconds. Thus the stimulation pulse duration $T_s$ should be kept below 0.5 milliseconds, but a shorter pulse will be more advantageous since the recovery time increases with the electrical charge of the pulse.

Another reason for using high amplitude narrow stimulating pulses is that the biphasic waveform duration consists not only of the stimulus duration $T_s$, but also the duration $T_c$ of the compensation pulse. To minimize the increase in the negative phase, the compensation pulse should be of low amplitude and relatively long duration. If the maximum stimulus of the standard pacer is used, for example, 12 milliamps for two milliseconds, the duration of compensation $T_c$ will become 20 milliseconds and this will be much too wide.

Figure 2:
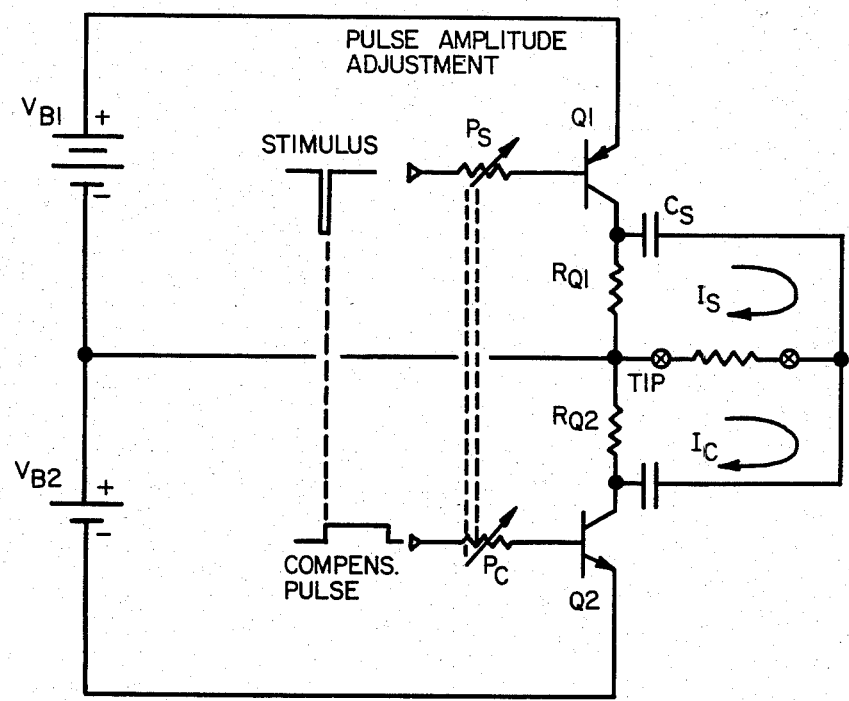
FIG. 2 is a schematic circuit diagram of an output stage used in the cardiac pacer of the present invention.

Referring now to FIG. 2, an illustrative embodiment of the output stage is shown therein. In this embodiment, there is one transistor for each portion of the biphasic waveform as well as two power supplies (or a tapped single power supply).

Transistor $Q_1$ produces the stimulus running conventionally from the lead's ring or pacer's case to the tip while transistor $Q_2$ produces the compensation pulse running from the lead's tip to the ring or pacer's case.

Potentiometers $P_s$ and $P_c$ adjust stimultaneously the output of each pulse, keeping a relative constant ratio between them at any output value.

One may notice that for high current amplitudes the output stage $Q_1$ from FIG. 2 does not provide sufficient current regulation with load variation. However, stage $Q_2$, delivering less than 3 mA, will provide good regulation.

To obtain a stimulus with big amplitude, for example 30 mA, on a 200 to 700 ohm load, the battery $V_{B1}$ must supply a voltage of more than 25 V while $V_{B2}$ still has to supply only 6–7 V. A 30 volt battery able to supply currents in the order of 30 mA is bulky and difficult to manufacture.

We have found that a better solution is to build a voltage multiplier for $V_{B1}$ and to use the pacer's battery itself as $V_{B2}$. There are different schematics for voltage multipliers. An example is presented in FIG. 3.

The four equivalent switches from CD-4013 switch successively, charging the one microfarad capacitors with the voltages shown in the figure and finally adding their voltage and building up a total voltage of $V_{B1}=4 V_B$. This voltage charges the 200 microfarad capacitor converting the high voltage in a quantum of charge which, pumped with a frequency of 16000 quanta/sec, changes this capacitor also to the $4 V_B$ voltage.

Figure 3:
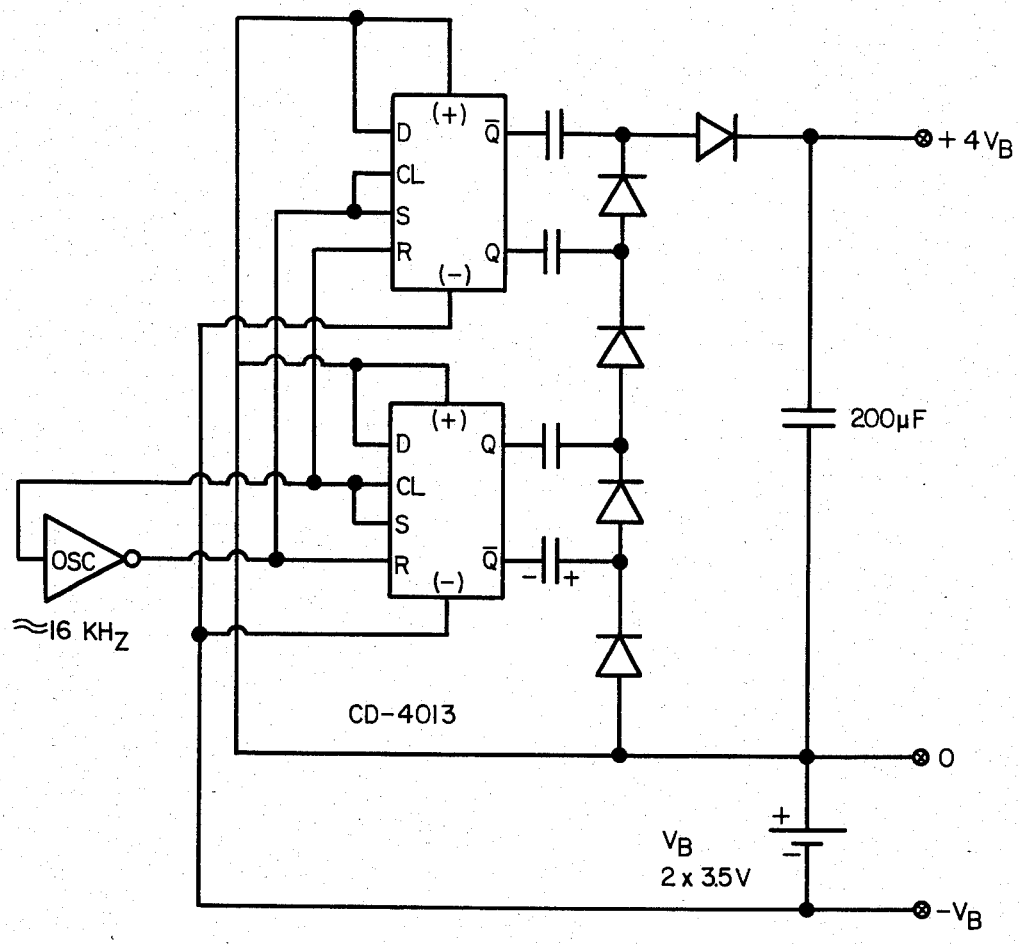
FIG. 3 is a schematic circuit diagram of a power supply used in the cardiac pacer of the present invention.

As it can be seen from FIG. 3, choosing the positive terminal of the battery as a reference bar, the battery itself can be used as a negative voltage while the multiplied voltage is the positive one.

Figure 4:
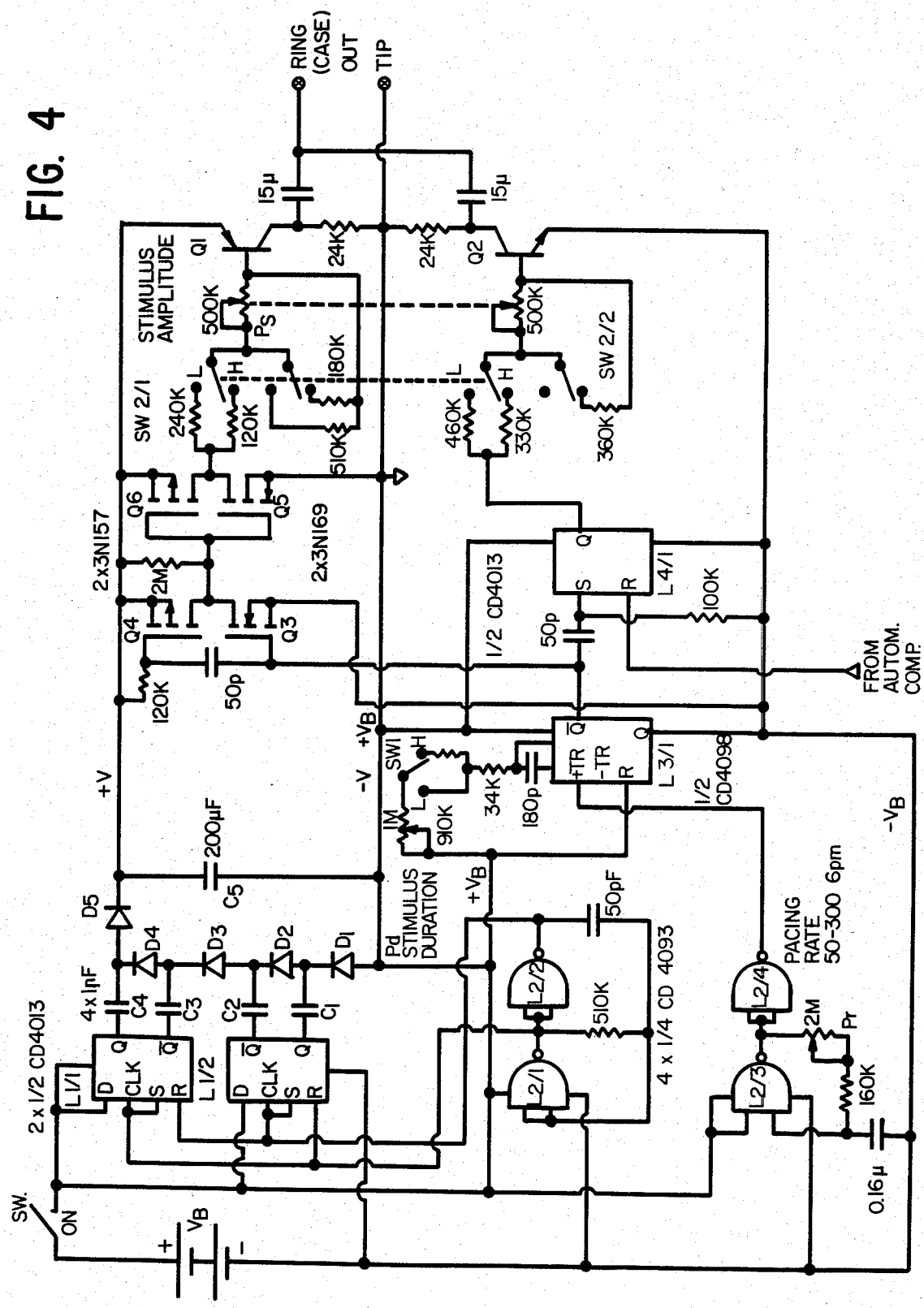
FIG. 4 is a schematic circuit diagram of the logic circuitry used in the cardiac pacer of the present invention.

One example of a logic circuit of the cardiac pacer is illustrated in FIG. 4. The oscillator L 2/3–L 2/4 provides a succession of pulses with adjustable rate. The leading edge of each pulse triggers the monostable L 3/1 which resets after an interval set by switch $SW_1$ and potentiometer $P_d$. This circuit sets the duration of the stimulation pulse, the output of L 3/1 triggers the $Q_1$ output stage.

Transistors $Q_3$–$Q_6$ provide the interface between $Q_1$ supplied with the voltage V (approximately 26 V) and the monostable L 3/1 supplied with the voltage $V_B$ (7 V).

At the end of the interval set by $SW1/P_d$ the output Q of the monostable L 3/1 sets the latch L 4/1 which now triggers the output stage $Q_2$. The reset of latch L 4/1 is the end of the compensation pulse and it is determined by the circuit called "Automatic Compensation." Transistor $Q_2$ will be kept ON for a duration correlated with the charge delivered by the stimulation pulse and the amplitude of the compensation pulse.

As stated above, for a fast recovery after a pacer stimulus, the charges provided by the two components of the biphasic waveform must be equal. This can be achieved with a constant ratio between the amplitudes and respectively the durations of the two pulses.

It is difficult to program accurately the amplitudes and duration of the two pulses with a simultaneous maneuver for the necessary range. The stimulation pulse is not constant with load variation, while the compensation pulse is. At very narrow stimulation pulses the distortion of the stimulus will be different from that of the compensation pulse. As a consequence, the biphasic waveform must be dynamically balanced.

Figure 5:
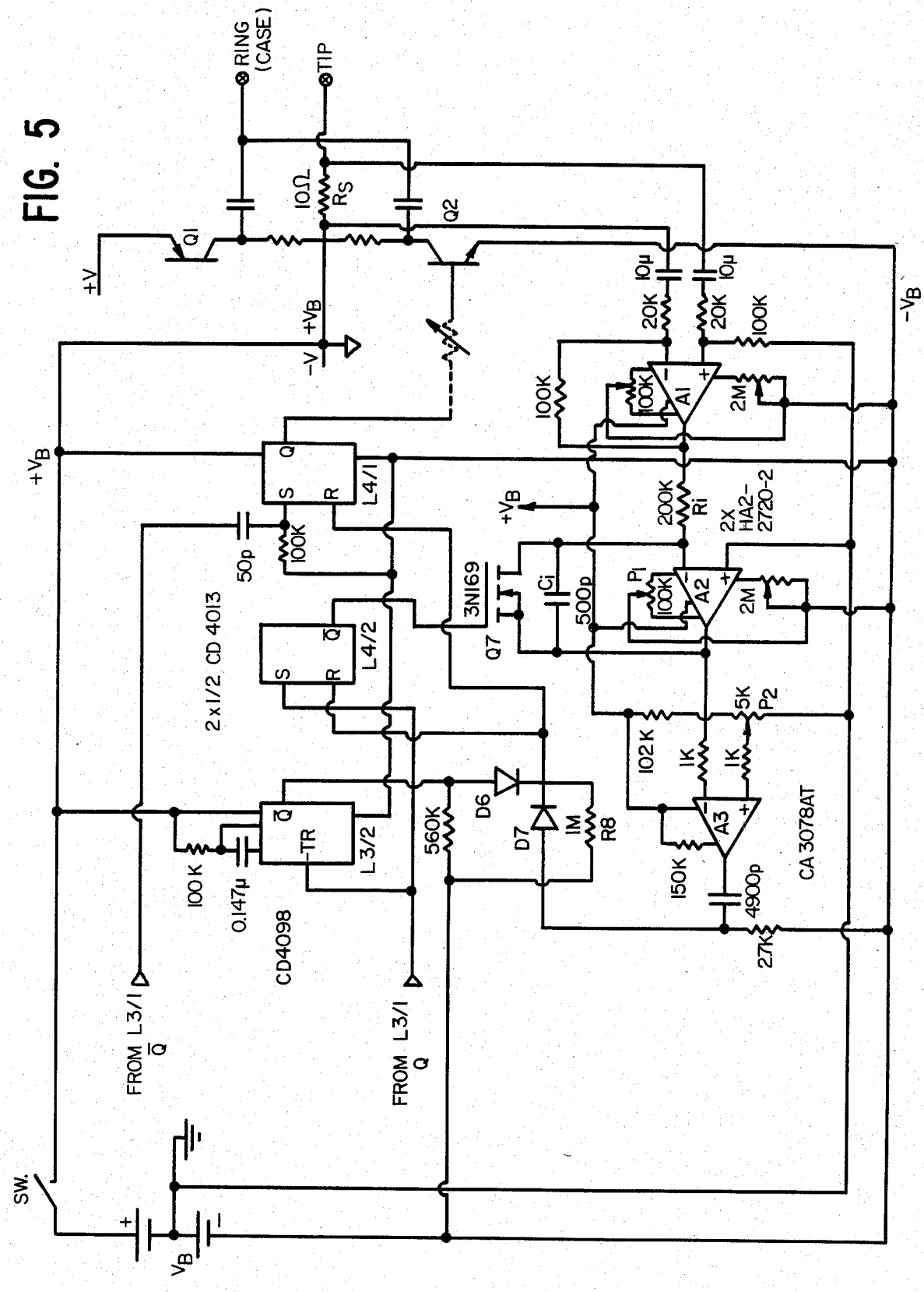
FIG. 5 is a schematic circuit diagram of an automatic compensation circuit used in the cardiac pacer of the present invention.

The circuit for automatic and dynamic compensation is shown in FIG. 5. The key of the circuit is integrator A2. The integrator integrates successively the stimulus and the compensation pulse. The two integrals must be equal for perfect compensation.

Through a 10 ohm resistor ($R_s$) in series with the load circuit, an input voltage proportional to $I_s$ and $I_c$ is applied to the differential amplifier A1. The amplified signal is then integrated by A2. When the equal charge condition is enforced, the null detector A3 switches and resets the two latches L 4/1 and L 4/2. This action ends the compensation pulse as it turns off output stage $Q_2$.

Between two successive output pulses, the integrator is kept in a reset state by transistor $Q_7$. If the integration of $I_c$ cannot be accomplished, e.g., if the leads are disconnected from the load, the circuit can latch up (the integrator is no longer reset). To prevent this, monostable L 3/2 issues a reset pulse 6 ms after the stimulus is initiated. The wired OR ($D_6$, $D_7$, $R_g$) allows the reset of L 4/2 ( and L 4/1) by the first pulse: the integrator's zero detector pulse from A3 or the delatching pulse from L 3/2.

We have found that the detection in the ventricle of the evoked QRS, rather than the T wave, is most suitable for capture detection. The amplitude of the QRS complex for pervenous leads is at least 10 mV. For the atrium, the evoked P wave can be as small as 2 mV. For both chambers, the delay from stimulus to the first peak is at least 10 ms and the whole pulse duration is no longer than 70 ms for the ventricle (QRS only) and 25 ms for the atrium.

Other automatic charge compensation methods may be used. The stimulating pulse and the compensating pulse may be of preset duration, but the amplitude of the compensating pulse would follow the amplitude of the stimulating pulse. The stimulating pulse would be sampled and its amplitude at each sample would be stored. The compensating pulse would then be constructed by issuing ten samples for each stimulus sample at 0.1 times its amplitude. The compensating pulse, having an accurate preset duration of ten times the stimulating pulse duration, will also simulate the stimulus amplitude at 0.1 times it amplitude. This method can be implemented, for example, in a microprocessor-based pacemaker.

Figure 6:
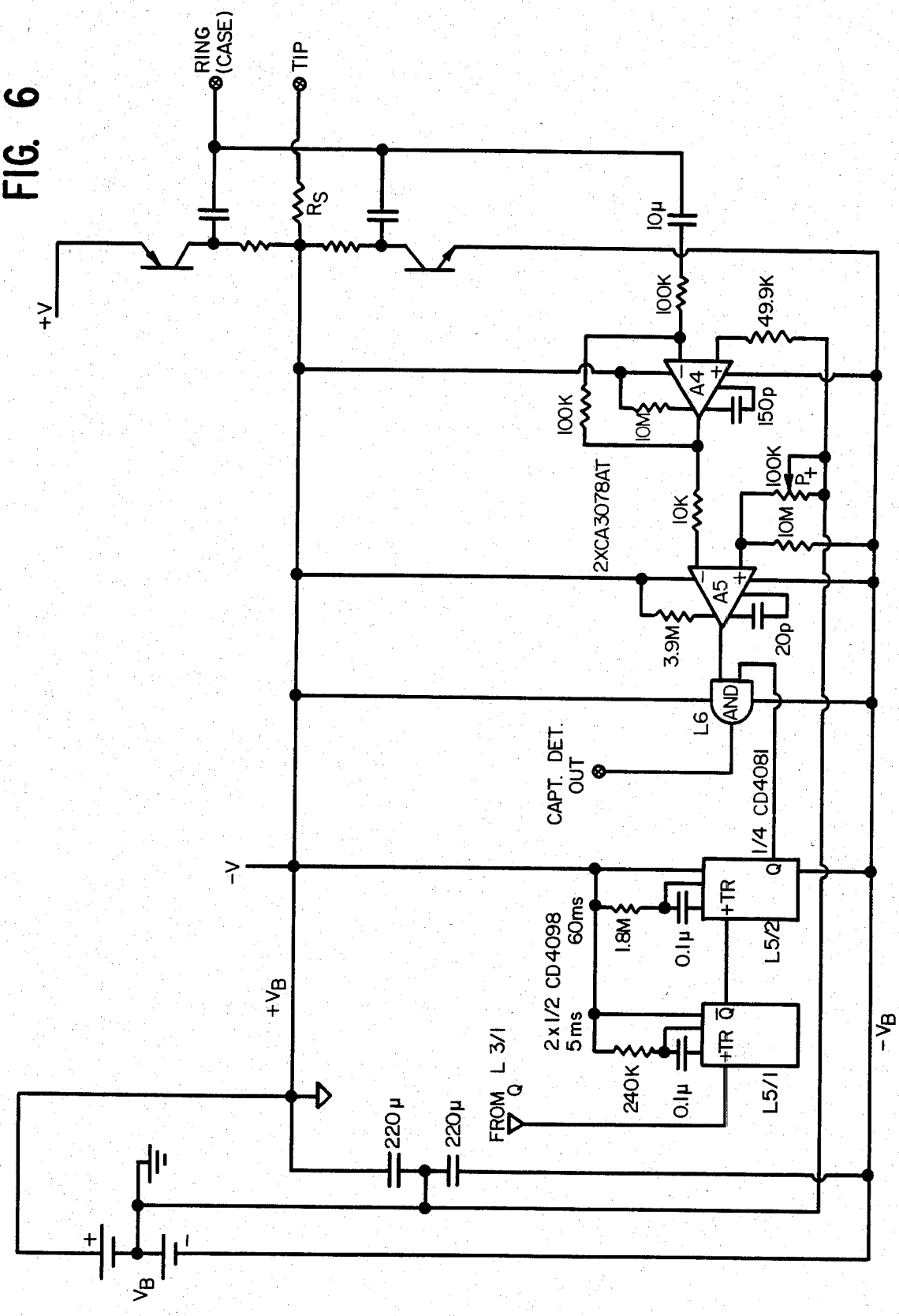
FIG. 6 is a schematic circuit diagram of a capture detector used in accordance with the principles of the present invention.

A capture detection circuit is illustrated in FIG. 6.

The electrical activity across the pacer lead is picked up by amplifier A4 connected between the "ring" and the tapped battery (which from the AC point of view is connected to the "). The CA 3078 amplifier has a relatively narrow band-pass so the ringing of A4 after an almost 20 V input from the narrow stimulus is limited in effect, becoming ineffective in less than 5 ms. The amplifier A4 while shown as a single-ended amplifier could also take the form of a differential amplifier with the inputs connected across the 10 ohm resistor Rs.

The monostable L 5/1 triggered by L 3/1 simultaneously with the onset of the stimulation pulse, blanks the output of the capture detector for 5 ms after the stimulus is issued. This interval allows the amplifier to recover into the ineffective limits. After 5 ms, monostable L 5/2 is triggered and its output, connected to the input of the AND gate, now allows the detection of any heart activity. L 5/2 stays with its Q output high for about 60 ms and then resets. If during the time-window created by the two monostables L 5/1 and L 5/2, an evoked response exists and comparator A5 is triggered, gate L6 will issue a positive output pulse.

The threshold of comparator A5 is adjusted with potentiometer $P_t$, as it needs to be different for the atrium and for the ventricle.

The technique described above allows the detection of capture and then provides information for threshold searching. The evoked response is recovered from its very onset, without significant distortions due to electrode recovery; it can be further studied for location and morphology. The evoked response may carry information about the need of the patient for adjustment in pacing rate and about capture with stimuli that have too large a charge. Rate and threshold adjustments can be suitably made in response to this information.

Although it it not believed to be essential to the disclosure of the invention, a circuit diagram containing the circuits of FIGS. 2-6 connected together, is attached to this application as Appendix A. However, subject to the Examiner's approval this paragraph and the Appendix may be excised from the portion of the application that is published.

Although an illustrative embodiment of the invention has been shown and described, it is to be understood that various modifications and substitutions may be made by those skilled in the art without departing from the novel spirit and scope of the present invention.

What is claimed is:

1. A method of detecting evoked response from the heart, comprising the steps of:
    providing a rectangular stimulating pulse;
    determining the charge of the stimulation pulse;
    thereafter generating a rectangular compensating pulse having an opposite polarity to the stimulating pulse and having an absolute amplitude that is less than the absolute amplitude of the stimulating pulse and having a duration that is continued during the generation of the compensating pulse until the charge of the compensating pulse is equal to the charge of the stimulating pulse; and
    thereafter detecting the evoked response using the same electrodes that are used for providing the stimulating and compensating pulses.

2. A method as described in claim 1, wherein the charge of the stimulating pulse is determined by integrating the stimulating pulse and the charge of the compensating pulse is determined by integrating the compensating pulse and generating the compensating pulse until the integral of the compensating pulse equals the integral of the stimulating pulse.

3. A method as described in claim 1, in which the stimulating pulse is a negative pulse and has a duration that is substantially less than the duration of the compensating pulse.

4. A method as described in claim 1, in which the charge of the compensation pulse is equalized to the charge of the stimulation pulse by providing a stimulation pulse of preset duration, sampling the stimulation pulse, storing the stimulation pulse amplitude at each sample, constructing the compensating pulse by issuing n samples for each stimulation pulse sample at 1/n times its amplitude.

5. A method as described in claim 1, in which capture is detected by blanking the output of a capture detector for a predetermined time after the stimulating pulse is issued, and thereafter providing a time window for seeking an evoked response.

6. A method as described in claim 1, in which the stimulation pulse is provided by multiplying the pacer's battery voltage using a voltage multiplier.

7. A method as described in claim 1, in which equal charges for any ratio between the amplitudes of the stimulating pulse and the compensating pulse are automatically provided.

8. A cardiac pacer in which stimulating pulses may be provided to a chamber of the heart via a stimulating electrode connected to the heart, which comprises:
    means for providing a rectangular stimulating pulse to said electrode;
    means for determining the charge of the stimulation pulse;
    means for thereafter generating a rectangular compensating pulse to said electrode, said compensating pulse having an opposite polarity to the stimulating pulse and having an absolute amplitude that is less than the absolute amplitude of the stimulating pulse and having a duration that is continued during the generation of the compensating pulse until the charge of the compensating pulse is equal to the charge of the stimulating pulse; and means for thereafter detecting the evoked response using the same electrodes that are used for providing the stimulating and compensating pulses.

9. A cardiac pacer as described in claim 8, in which the stimulating pulse is a negative pulse, and has a duration that is substantially less than the duration of the compensating pulse.

10. A cardiac pacer as described in claim 8, including means for integrating successively the stimulation pulse and the compensating pulse for equalizing the charge of the compensating pulse to the charge of the stimulation pulse.

11. A cardiac pacer as described in claim 8, including a capture detector, said capture detector having means for providing a time window for seeking an evoked response, said time window being set to commence subsequent to the trailing edge of the compensating pulse.

12. A cardiac detector as described in claim 8, in which the pacer includes a battery power source, and including a voltage multiplier for increasing the voltage applied to the stimulation pulse providing means.

13. A cardiac pacer as described in claim 8, including means for dynamically providing equal charges for any ratio between the amplitudes of the stimulating pulse and the compensating pulse.

* * * * *